United States Patent [19]

Schmer

[11] 4,438,198

[45] Mar. 20, 1984

[54] BIOCHEMICALLY ACTIVE MATRIX FOR USE IN A BIO-ARTIFICIAL ORGAN

[75] Inventor: Gottfried Schmer, Seattle, Wash.

[73] Assignee: Trimedyne, Inc., Arlington Heights, Ill.

[21] Appl. No.: 307,073

[22] Filed: Sep. 30, 1981

[51] Int. Cl.$^3$ .................. C12N 11/10; C12N 11/02; C12N 11/06; C12M 1/40
[52] U.S. Cl. .................................. 435/178; 210/927; 435/69; 435/176; 435/177; 435/180; 435/181; 435/229; 435/288
[58] Field of Search ............... 435/174, 176, 177, 178, 435/180, 181, 182, 288, 229, 69; 210/927

[56] References Cited

U.S. PATENT DOCUMENTS 3,639,558  2/1972  Csizmas et al. ................ 435/177 X

FOREIGN PATENT DOCUMENTS 49-41584  4/1974  Japan .

OTHER PUBLICATIONS

Dillon et al., Enzyme Immobilization on Fibrin, Chemical Abstracts, vol. 84:117768g, 1976, (p. 210).
Jackson et al., A New Extracorporeal Reactor-Dialyzer for Enzyme Therapy Using Immobilized L-Asparaginase, The Journal of Pharmacobogy and Experimental Therapeutics, vol. 209, No. 2, 1979, (pp. 271-274).
Zaborsky, O., Immobilized Enzymes, CRC Press, Cleveland, Ohio, 1973, (pp. 135-144).
Dillon et al., Enzyme Immobilization of Fibrin, Biotechnology and Bioengineering, vol. XVIII, 1976, (pp. 133-139).

*Primary Examiner*—David M. Nafe

[57] ABSTRACT

A biochemically active matrix for use in a bio-artificial organ is disclosed. The biochemically active matrix has an enzyme covalently bonded to a matrix of organochemically cross-linked fibrin. The matrix may be suspended in a medium of agarose which irreversibly solidifies below 37° C. The bio-artificial organ is useful for extracorporeal treatment of blood to remove excess substrate from the blood.

10 Claims, 5 Drawing Figures

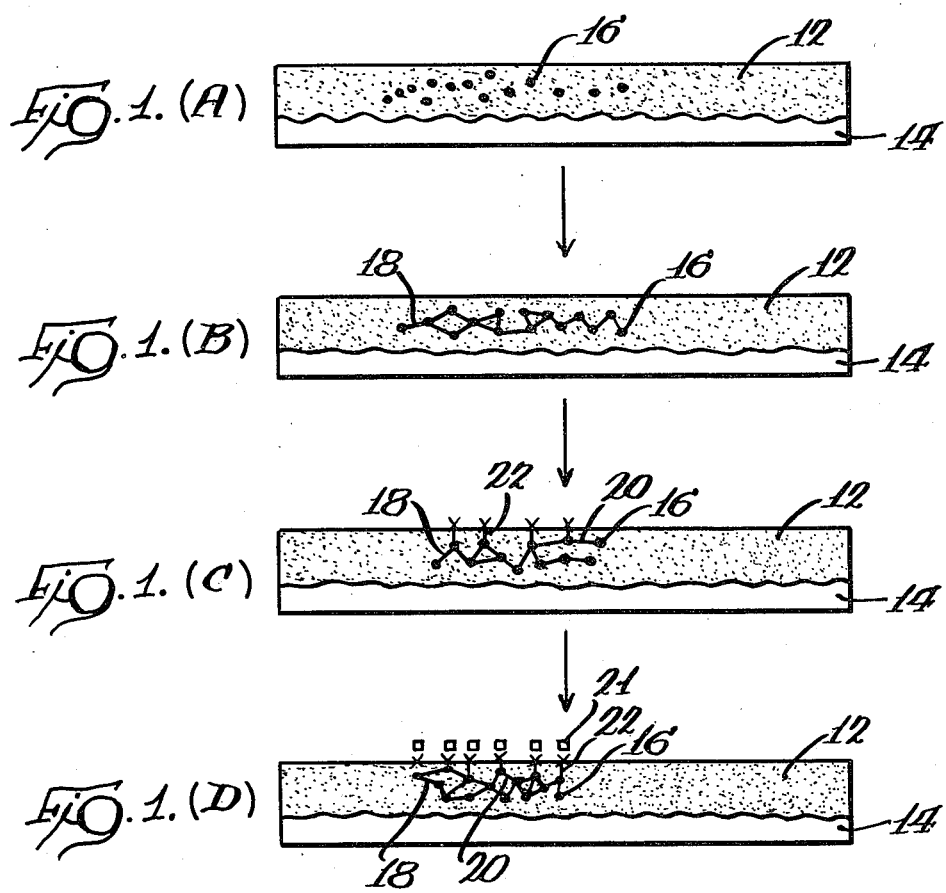
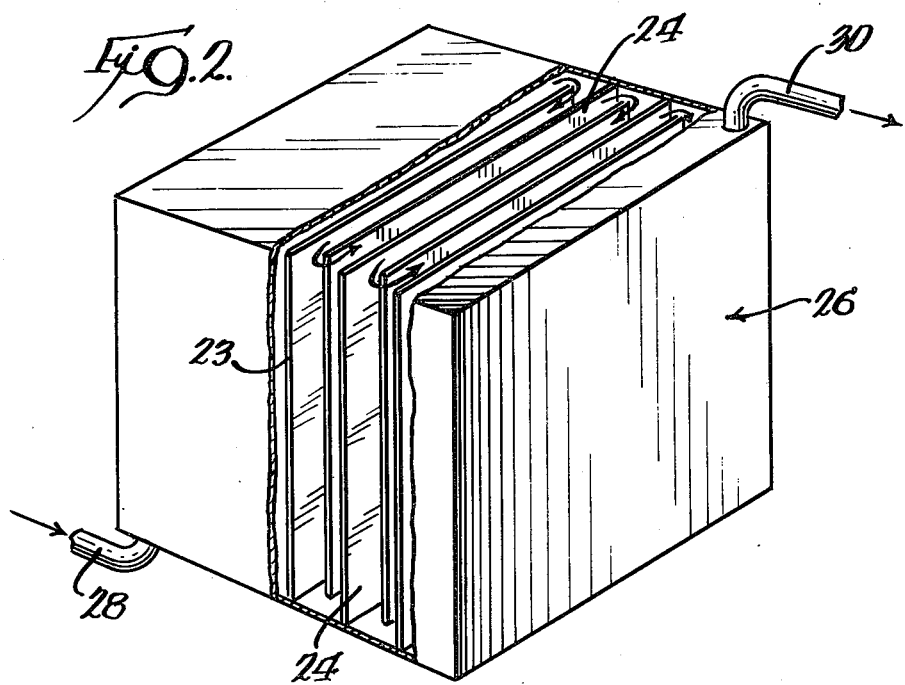

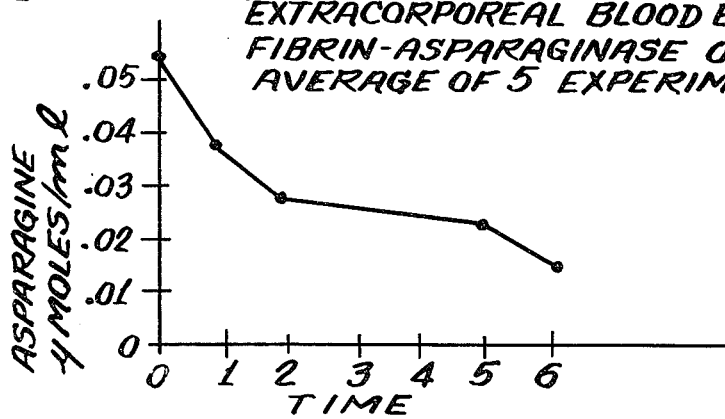
Fig. 3. DECREASE IN ASPARGINE LEVELS (μ MOLES/ml) IN SHEEP AFTER EXTRACORPOREAL BLOOD EXPOSURE TO FIBRIN-ASPARAGINASE ORGAN, AVERAGE OF 5 EXPERIMENTS.
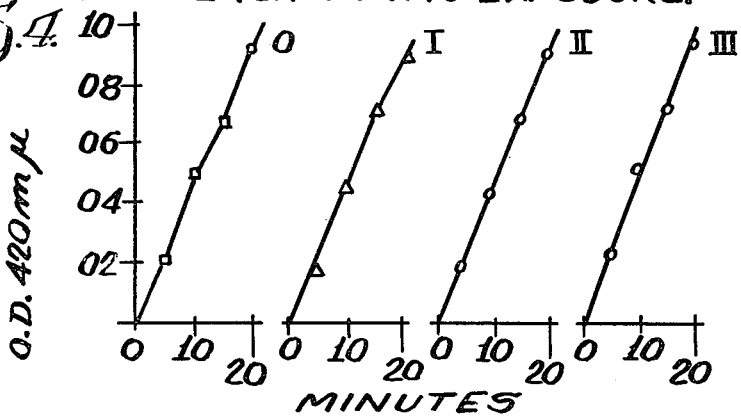
Fig. 4. IN VITRO TESTING OF FIBRIN-ASPARAGINASE ORGAN, BEFORE (0) AND AFTER (I, II, III,) EACH IN VIVO EXPOSURE.
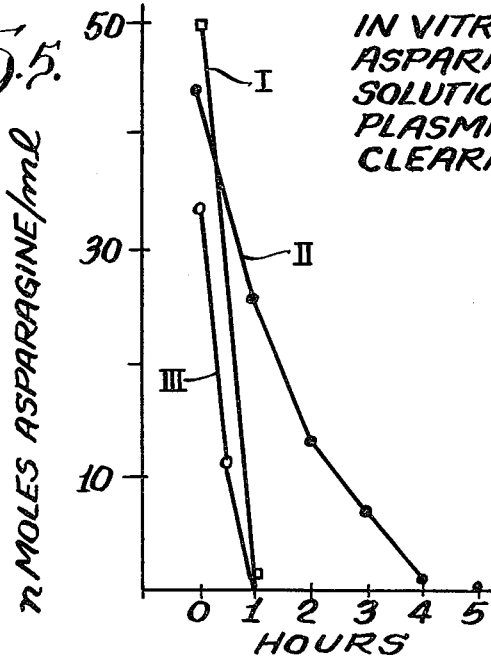
Fig. 5. IN VITRO CLEARANCE OF ASPARAGINE FROM AQUEOUS SOLUTION (IBS)(I), BOVINE PLASMA (III), AND IN VIVO CLEARANCE IN SHEEP (II).

// 1

BIOCHEMICALLY ACTIVE MATRIX FOR USE IN A BIO-ARTIFICIAL ORGAN

TECHNICAL FIELD OF THE INVENTION

This invention relates to bio-artificial organs, and in particular bio-artificial organs which utilize immobilized enzymes.

BACKGROUND OF THE INVENTION

In recent years, enzymes have been used for the treatment of blood to alleviate the symptoms of several diseases. However, the release of enzymes into the blood stream not only inhibits control over the amount of enzyme activity, but in case of some enzymes can also be toxic. To solve these problems, enzymes have been immobolized onto an insoluble matrix over which an extracorporal blood stream is passed over the matrix to allow the immobilized enzymes to act, such as by cleaving L-asparagine into ammonia and aspartic acid. Enzyme immobilization also has been shown to increase enzyme stability.

As a more specific example, the enzyme L-asparaginase, which hydrolyzes asparagine to aspartic acid and ammonia, has demonstrated antineoplastic activity in acute lymphocytic leukemia in man. The mechanism of the soluble enzyme's activity has been related to the depletion of blood L-asparagine levels resulting in the death of leukemic cells lacking endogenous synthetic capacity, for that amino acid. L-asparaginase has also been shown to have immunsuppressive properties and is useful as a treatment with on organ transplants. Unfortunately, free L-asparaginase has a variety of toxic side effects related to hypersensitivity and the inhibition of protein synthesis which precludes administration of the soluble enzyme by injection. Therefore, it is desirable to immobolize such an enzyme to obtain its useful properties while diminishing or eliminating its undesirable effects.

Attempts have been made for immobilizing biochemically active enzymes on or within various types of matrices using various types of linking agents. However, these attempts have not been entirely successful. Among the problems encountered are a short shelf life for the matrix bound enzyme, leakage of enzyme from the matrix, a low enzyme holding capacity for of certain supports such as silica, incompatibility with blood flow because of such problems as platelet aggregation, and reduced enzyme activity because of excessive linkage to the enzyme or interference of substrate and enzyme product flow through the matrix.

Excessive activation of the matrix by the linking agent increases the probability of multiple site bonding to the enzyme which quite frequently results in enzyme inactivation. Certain prior methods of retaining enzymes on a matrix have also resulted in large increase in the apparent Michaelis constant ("$K_M$"), indicating a substantial decrease in substrate affinity.

Accordingly, it would be desirable to provide a bio-artificial organ that avoids the deficiencies of the prior art and provides a biochemically active enzyme that remains active while being stably linked to a support matrix. The present invention provides such a bio-artificial organ.

SUMMARY OF THE INVENTION

The present invention relates to a bio-artificial organ, its method of manufacture and use. Utilizing the present invention an immobilized, biochemically active enzyme can be used to treat enzymic substrates within an extracorporeal stream or blood flow. The bio-artificial organ generally comprises a reactor housing for the passage of an extracorporeal blood stream or flow, and a biochemically active matrix located within the reactor housing and adapted to be placed in fluid contact with the blood stream or flow.

The biochemically active matrix is formed by covalently bonding at least one biochemically active enzyme to the surface of a carrier matrix. The carrier matrix is prepared by organochemically cross-linking fibrin. The carrier matrix can be retained on a physical support means or it may be formed (cast) on a solid support and then removed.

A biochemically active matrix on a physical support means defines a biochemically active member. The biochemically active matrix alone or as a biochemically active member is a biochemically active element and either type of element may be used in the organ.

The biochemically active member of the bio-artificial organ is prepared by coating a physical support means with a gel that includes hardened, biochemically cross-linked fibrin. The hardened fibrin is then organochemically cross-linked to form a matrix including organochemically cross-linked fibrin. A biochemically active enzyme is thereafter covalently bonded to the surface of matrix via a reactive group of the enzyme which is not essential for its enzymatic activity to form the completed biochemically active member.

Patients having an imbalance of an enzymatically degradable substrate in their blood can be treated by extracorporeal passage of their blood through a bio-artificial organ in accordance with the present invention. Within this organ the blood contacts the biochemically active matrix whereby the chosen enzyme reacts with the substrate present the blood. The blood so treated is then returned to the patient. When the terms substrate and enzyme are used in conjunction, they are to be understood as referring to an enzyme and its substrate.

The present invention provides several benefits and advantages. The organochemically cross-linked fibrin is particularly useful as a matrix because of its good mechanical stability towards flowing blood and its biocompatability with blood. Organochemically cross-linked fibrin provides micro environment which preserves and stabilizes the matrix-bound enzymes. Because the hardened fibrin is organochemically cross-linked and the excess cross-linking agent is removed before the biochemically active enzyme is introduced, excessive cross-linking with the enzyme is avoided as well as the usually inherent decreases in or elimination of enzyme activity. This is unlike prior attempts wherein cross-linking agent was present while the enzyme was being linked onto a support matrix. This is particularly important with enzymes such as indolyl-3-alkane-α-hydroxylase wherein during previous studies up to 95 percent of the enzyme activity was lost during the enzyme-matrix bonding process.

The present invention also stabilizes the biochemically active enzymes and provides biochemically active matrices having a shelf life of several months at 4° C. High enzyme activity was exhibited in a fibrin-urease system after three weeks in the absence of ethylenediamine tetraacetate (EDTA). This was remarkable since previous experience indicated that it was difficult to stabilize and solubilize urease in the absence of EDTA.

Another advantage is that the matrix including organochemically cross-linked fibrin has been found to be substantially without effect on the platelet consumption of extracorporeal blood which passes over it. Also, fibrin can be used in the bio-artificial organ from sources other than the patient's blood with no immunological response.

Yet another benefit of this invention is that otherwise toxic or deleterious effect-causing free enzymes, such as L-asparaginase, can be utilized in immobilized form for their beneficial qualities while their otherwise undesirable deleterious qualities are minimized or substantially eliminated.

Still another benefit of this invention is that a bio-artificial organ can be prepared which contains a plurality of active members, one or more of which includes one or more different, covalently bonded enzymes so that more than one enzymatic reaction can be carried out while blood passes through the bio-artificial organ. This minimizes the number of extracorporeal passages and the time needed to carry out the desired enzymatic reactions.

Further benefits and advantages of the instant invention will become apparent to those skilled in the art from the detailed description which follows.

BRIEF DESCRIPTION OF THE DRAWINGS

FIG. 1 is a schematic representation showing the process of preparing a matrix and grafting enzymes thereon;

FIG. 2 is a perspective fragmentary view showing a bio-artificial organ of the present invention including a reactor housing and a plurality of physically supported, enzyme-bearing, matrices within the reactor housing;

FIG. 3 is a graph showing the decrease in asparagine levels in sheep during treatment with a bio-artificial organ of the present invention;

FIG. 4 is a set of graphs showing test results of a bio-artificial organ of this invention before and after in vivo tests; and FIG. 5 is a graph showing the clearance of asparagine from different solutions using a bio-artificial organ of this invention.

DETAILED DESCRIPTION OF THE PREFERRED EMBODIMENTS

The bio-artificial organ of the present invention generally comprises at least one biochemically active enzyme covalently bonded to the surface of a matrix of organochemically cross-linked fibrin. Fibrin is a cross-linked, gelled protein formed by the biochemical cross-linking reaction of fibrinogen by thrombin to form a soft clot (fibrin gel). The fibrin is then treated with Factor XIII together with thrombin and calcium ions ($Ca^{+2}$) to form a hard clot, also referred to as hardened, biochemically cross-linked fibrin. Fibrinogen, thrombin and Factor XIII are found in and isolated from the blood of humans and other warm-blooded animals. The hardened, biochemically cross-linked fibrin is further cross-linked organochemically, by one or more chemical cross-linking agents, as will be discussed in greater detail below to form a matrix. A biochemically active enzyme is then covalently bonded to the surface of the matrix. The enzyme utilized can be any enzyme suitable for treatment of an extracorporeal blood flow. Examples of suitable enzymes are also discussed below.

In one embodiment, the matrix is prepared by admixing a solution containing clottable fibrinogen together with a solution containing thrombin to form an admixture of solutions. The term "solution" as used herein is to be understood as applying both to true solutions and to suspensions. The admixing of solutions is preferably conducted at room temperature (20°–25° C.).

The fibrinogen solution can contain about 15 to about 35 milligrams of fibrinogen per milliter of solution, and preferably contains about 30 milligrams of fibrinogen per milliliter of solution. The fibrinogen solution also preferably contains a physiological amount of sodium chloride (saline) and more preferably imidazole buffered saline (IBS), e.g., 0.15 M NaCl plus 0.02 M imidazole, either solution being buffered at approximately pH 7, and preferably at pH 7.35. Human, bovine, porcine, and similar clottable fibrinogens are useful.

The thrombin solution can contain about 50 to about 150 units of thrombin per milliliter, and preferably about 90 to 110 units of thrombin per milliliter of saline, or optimally IBS. Preferably about 0.015 to about 0.025 units of thrombin are present in the resulting admixture for each milligram of fibrinogen, with an optimal proportion being about 60 milligrams of fibrinogen per unit of thrombin. Thrombin from human, bovine, porcine, and similar sources is useful.

This resulting admixture is then spread, preferably immediately, on a biologically compatible physical support means and the fibrinogen is converted into fibrin. The physical support means is compatible with the components of the admixed solutions and with the extracorporeal blood stream. The physical support means preferably is a roughened glass plate pretreated or coated to substantially prevent clotting. A particularly preferred coating can be prepared from a dilute solution of agarose (SeaKem) (e.g. 0.5 percent by weight in water). SeaKem is a trade designation for an agarose powder available from Marine Colloids, Inc., Rockland, Me.

Any convenient size of physical support means can be utilized. In one particularly preferred embodiment of this invention, glass plates were used which had dimensions of about 10×10×0.1 centimeters. In this particular embodiment, the plates were first cleaned with nitric acid and then coated with a solution of agarose (0.5 weight percent) as is conventionally used to prevent clotting. The surface of the glass plate was roughened, as by sand blasting, etching or the like, so that the agarose coating adheres more firmly to the glass and serves as a "primer" coat to assist adherence of the fibrin matrix to the glass.

In addition to glass, the physical support means can be made from a variety of materials. Examples of such materials include, but are not limited to, metals such as stainless steel, and plastics such as poly(ethylene), poly(propylene), copolymers of ethylene and propylene alone or with additional monomers such as vinyl acetate, fluorinated polyolefins such as poly(tetrafluoroethylene), and the like as are used in the medical implant arts.

Specific examples are the polymers sold under the trademark designation MICROTHENE MN 718 and MICROTHENE MN 786 sold by U.S. Industrial Chemicals Company. Illustrative homopoly(propylene) polymers useful herein include the polymer sold by Eastman Chemicals under the trade designation 4250G and that material sold by Hercules, Inc. under the designation 6301. An example of an ethylene-propylene thermoplastic elastomer useful herein is that material sold by Exxon Chemical Co., U.S.A. under the designation Vistalon-702. A particularly preferred ethylene-vinyl acetate copolymer is sold under the trademark designation MICROTHENE MU 763.

The criteria for the physical support means are that it be capable of supporting the matrix, and be compatible, either alone or after suitable treatment, with the other components of the biochemically active member and the extracorporeal blood flow. The physical support also preferably has a roughened surface. The support can be in the form of plates, beads, tubes, permeable or semipermeable membranes or the like.

Fibrin is then allowed to polymerize, preferably for about 15 minutes, at about room temperature. This is shown schemetically in FIG. 1, Diagram A, wherein the fibrin molecules form a soft clot gel 12 on the surface of a roughened glass plate 14. In FIG. 1, individual fibrin molecules are schematically depicted as dots 16. The other side of the solid support or glass plate may also be similarly coated with a polymerized fibrin gel.

In another embodiment, an initial gel can be prepared by mixing a solution containing clottable fibrinogen and a polysaccharide. Preferably, the polysaccharide is an agarose which irreversibly gels below a given temperature such as about 37 degrees C. Such an agarose is commercially available as "Low Gel Temperature Agarose" from Biorad Laboratories of Richmond, Calif. Other possible polysaccharides are cross-linked heparin, cross-linked mucopolysaccharide as well as any polymers of neutral sugars.

In this embodiment, a solution containing about 30 to about 60 milligrams, and preferably about 45 milligrams of fibrinogen per milliliter of solution is prepared and warmed to a temperature above that at which the agarose irreversibly gels. The fibrinogen is preferably in a solution of IBS. A second solution containing about 20 milligrams to about 50 milligrams of agarose per milliliter of solution, preferably IBS, is prepared, with an optimal amount of about 4 weight percent in IBS. The agarose solution is preferably heated to a temperature of about 60° C. to about 100° C., and optimally about 80° C. and then cooled to a temperature that is still above that at which the gel irreversibly gels. The polysaccharides useful herein preferably gel irreversibly below about 40° C. It is to be noted that this agarose solution can be different from that used in the priming coat for the glass plate, i.e., it can be a different concentration or even a different type of agarose. Additional layers as descibed are deposited upon the priming coat, rather than embedded in it.

About 1 to about 2 parts of fibrinogen solution are then thoroughly admixed with about 1 part of agarose solution to provide a fibrinogen-to-agarose weight ratio of preferably about 1:1 to about 2:1. Although the weight of the fibrinogen can be greater than the agarose, the agarose is in a swollen state and, thereby occupies a greater volume per unit weight. The fibrinogen is suspended within the resulting admixed composition. Similarly, when the fibrinogen is converted into fibrin, the fibrin is suspended in an agarose medium. Mixing is typically carried out for about 5 minutes while maintaining the resulting composition above the temperature of irreversible gellation, e.g., about 38° to about 40° C. The compostion is then spread on a physical support means such as the above discribed glass plate, which is preferably prewarmed to about 37° C. The other side of the glass plate can also be coated, either separately or both sides of the plate can be coated substantially simultaneously as by dipping into the composition. The fibrinogen-agarose composition then permitted to gel.

The gelled composition is then soaked, preferably for about 1 hour at room temperature, in an aqueous solution containing sufficient thrombin to convert the fibrinogen into fibrin and form a soft clot fibrin-agarose gel. The fibrinogen has sufficient mobility to permit reaction with thrombin for conversion into fibrin and cross-linking the fibrin into a soft clot. The solidified composition has sufficient permeability to permit entry and reaction of thrombin and other molecules (e.g., Factor XIII and glutaraldehyde as discussed below) to further biochemically and organochemically cross-link the fibrin.

The remaining steps are the same for both of the above described gels, i.e., the soft clot fibrin gel and the soft clot fibrin-agarose gel. The gels can be coated upon the glass plate as described above. If desired, however, the gel may be removed from the physical support means and treated as set out below to prepare a biochemically active matrix which is self-supporting, i.e., not mounted on a support.

The gel is then soaked in a solution containing Factor XIII, thrombin, and calcium ions ($Ca^{+2}$) to biochemically cross-link the fibrin within the gel. This is shown schematically in FIG. 1, Diagram B, where Factor XIIIa 18 (the reaction product of Factor XIII reacted with thrombin) biochemically cross-links fibrin molecules 16. This solution preferrably comprises heat defibrinated (57° C. for 3 minutes) citrated plasma, recalcified with $CaCl_2$, as is known in the art, and 20 units of thrombin per milliliter of plasma. Generally, the Factor XIII solution must also contain calcium ions ($Ca^{+2}$) and thrombin to biochemically cross-link the fibrin from a soft clot to a hard clot. This biochemical cross-linking typically takes place over a period of 4–6 hours at room temperature and stabilizes the fibrin. The plate is then washed to remove excess reagents.

The fibrin amino groups which have not previously formed biochemical cross-links are then reacted with an organochemical cross-linking agent to make the hardened fibrin resistant to fibrinolysis, and to consume amino groups which otherwise might cause clotting of the extracorporeal blood stream. Reaction with the organochemical cross-linking agent provides a carrier matrix having sites for covalent bonding a biochemically active enzyme.

The organochemical cross-linking agent can be any suitable molecule for cross-linking protein amino groups. Suitable organochemical cross-linking agents include dialdehydes containing up to 10 carbon atoms, such as glutaraldehyde and terephthaldehyde, cyanuric chloride, cyclic anhydrides containing 4–9 carbon atoms, such as succinic anhydride, maleic anhydride, and adipic anhydride, activated dicarboxylic acid esters which contain 2–8 carbon atoms in the dicarboxylic acid, such as
bis(salicyl)succinate,
bis(3,5-dibromosalicyl)fumarate,
bis(3,5-dibromosalicyl)terephthalate,
bis(N-hydroxysuccinimido)adipate, and the like.
Glutaraldehyde is the preferred organochemical cross-linking agent.

With glutaraldehyde, it is preferred that the amino groups on the fibrin be reacted with an aqueous solution containing about 2.5–10 percent by volume glutaraldehyde and having a pH value of about 7.3 to about 7.5.

The presence of phosphate ion (0.1 M $PO_4^{-4}$) is also beneficial. For glutaraldehyde, the cross-linking reaction is usually carried out at room temperature over a period of about two to four hours. Cyclic anhydrides containing 4 to 8 carbon atoms are preferably utilized in an aqueous solution at about 1 weight percent and a pH value of about 6 followed by reaction with a water-soluble carbodiimide such as 1-ethyl-3-(3-dimethylaminopropyl)carbodiimide hydrochloride at a pH value of about 5–6. The activated dicarboxylic acid esters are dissolved in an aqueous solution buffered at about pH 7–7.5; a 0.1 M TRIS-HCl [tris(hydroxymethyl) amino ethane hydrochloride] buffer being exemplary.

Each of the above-discussed organochemical cross-linking agents and the cross-linking reactions are known in the art and will not be discussed further herein.

After the organochemically cross-linked carrier matrix is formed from a hard clot, a biochemically active enzyme is covalently bonded to the surface of the carrier matrix through a reactive group of the enzyme which is not essential for its enzymatic activity. In preferred practice, a sufficient amount of the organochemical cross-linking agent is added to react with substantially all of the remaining fibrin-amino groups to form organochemical cross-links, and to also provide linking arms, pendant from the matrix for covalently bonding the biochemically active enzyme to the matrix produced. However, organochemical cross-linking and pendant enzyme-linking arm formation of the carrier matrix may be independent. Still further, a biochemically active enzyme covalently bonded to a linking arm of its own can be covalently bonded to the surface of the carrier matrix. Use of the preferred organochemical cross-linking agent, glutaraldehyde, is schematically shown in FIG. 1, Diagram C wherein a portion of the glutaraldehyde 20 cross-links amino groups of the fibrin which have not previously biochemically cross-linked while another portion of the glutaraldehyde 22 only links one aldehyde group with a fibrin amino group leaving an aldehyde containing arm free to form a covalent bond with a subsequently introduced amino group-containing molecule, such as an enzyme. FIG. 1, Diagram C shows the plate mounted carrier matrix prepared for linking with an enzyme to form a biochemically active matrix.

After the hard clotted fibrin has been organochemically cross-linked and the enzyme-linking arms formed, the matrix is washed to remove any excess cross-linking agent. The matrix is then contacted with a solution containing at least one biochemically active enzyme so that the enzyme reacts with the linking agent arms to covalently bond the enzyme to the surface of the carrier matrix and form a biochemically active matrix. The biochemically active matrix when mounted on a physical support means, such as the glass plate 14 shown in FIG. 1, Diagram D, is refered to as a biochemically active member.

In FIG. 1, Diagram D wherein the enzyme schematically represented by squares 21 is covalently bonded to the individual arms of the glutaraldehyde molecules 22. An excess of biochemically active enzyme is provided to help assure substantially complete reaction with the free cross-linking arms. The biochemically active enzyme can be urease, L-asparaginase, L-glutaminase, indolyl-3-alkane-α-hydroxylase or any other enzyme suitable for the treatment of blood by reaction with blood-contained substrates.

Although the previous discussion has dealt with the formation of enzyme-matrix covalent bonding via the preferred reaction with a free-linking arm of a partially reacted organochemical cross-linking agent, additional means of affixing the enzyme to the matrix are known and can be utilized. In these reactions, it is presumed that the free linking arms of the organochemical cross-linking agent are not present. It is noted that agarose hydroxyl groups can interfere with covalent bonding of the enzyme to the matrix for those embodiments of this invention wherein the matrix is suspended in an irreversibly gelled agarose medium. Thus, care should be taken in selecting enzyme-linking reactions to assure that the enzyme is bonded to the matrix and not to the agarose.

In one exemplary reaction, enzyme-amino groups are first N-acylated with an N-blocked amino acid containing 2–6 carbon atoms in the carboxylic acid, such as N-tert.-butyl-oxycarbonyl glycine (t-Boc glycine) or t-Boc 6-aminohexanoic acid, using a suitable activating agent such as dicyclohexyl-carbodiimide or the before named, water-soluble carbodiimide. The N-acylated enzyme so produced is then deblocked and reacted with a carboxy group of the matrix using the above-mentioned water-soluble carbodiimide. In another illustrative reaction, an N-blocked, activated amino acid ester having the above-stated carboxylic acid chain length, such as N-hydroxysuccinimido N'-t-Boc beta-alanine, is first reacted with an amino group of the enzyme, without carbodiimide activation, to form an N-acylated enzyme, thereafter which is deblocked and coupled to the matrix as described above. In yet another exemplary reaction, a diamine(primary or secondary), having 2–6 carbon atoms in the chain, such as ethylenediamine, cadaverine, N-methyl-1,3-propane-diamine and the like, is coupled with a matrix carboxy group and then with an enzyme carboxy group, both couplings utilizing a water-soluble carbodiimide for activation.

As discussed in conjunction with formation of the enzyme-matrix covalent bond via the partially reacted organochemical cross-linking reaction, the enzyme-matrix linking reactions are well-known in the protein modifying arts, and specific reactants and reaction conditions are readily available in the literature. In addition, it is emphasized that the enzyme-matrix covalent linking reactions discussed are illustrative and are not intended to be limiting.

In FIG. 2, the biochemically active matrix is mounted on glass plates 23 to form biochemically active members which are contained in a reactor housing. About twenty biochemically active members 24 are fixed as by insertion into grooves within a reactor housing 26 having an inlet 28 and an outlet 30 to form a bio-artificial organ. The inner surfaces of the reactor housing 26 should be compatible with an extracorporeal blood flow. As shown, the members 24 can be staggered to provide a blood flow over both sides of the members.

The produced organ can be sterilized in a solution of IBS which additionally contains 0.02 percent sodium azide and stored in that sterile solution at a temperature of about 4 degrees C. for a period of several months without substantial loss of biochemical activity. Prior to use, the organ is repeatedly flushed with sterile saline to remove any sodium azide. While sodium azide is a highly toxic material, repeated rinsing is effective because no toxic reactions were observed in the sheep tested. See Schmer et. al., Trans. Am. Soc. Artif. Intern. Organs, XXVI:129 (1980) and Schmer et. al., Int. J.

Artif. Organs, 4:96-101 (1981) both incorporated herein by reference.

The fibrin matrix proved not only compatible, but an effective matrix as well. No free asparaginase could be detected during in vivo or in vitro tests. These tests were made at flow rates of 150 to 200 milliliters/minute over a biochemically active member organ having an active surface area of about 4000 $cm^2$. However, at flow rates in excess of 300 milliliters/minute some leakage of L-asparaginase was observed, evidently caused by mechanical (shear stress) removal of fibrin particles containing the immobilized L-asparaginase.

EXAMPLE 1

Bio-artificial Organ Incuding L-Asparaginase Active Members 10 milliliter portions of bovine fibrinogen (30 milligrams lyophilized fibrinogen per milliliter of IBS at pH 7.35 commerically available as Pentex from Miles Laboratories, Elkhart, Ind.) was admixed with five units of crude bovine thrombin (Parke, Davis and Co., of Detroit, Mich., 1,000 units dissolved into 10 milliliters of IBS at pH 7.35) and the admixture spread immediately on one surface of roughened glass plates at room tempature (10×10×0.1 cm commercially available as Elphor plates from LKB Instruments, Inc. of Vincent, Calif.). The plates had been pre-treated by nitric acid and coating with 0.5 percent agarose. After about 15 minutes at room temperature, the resulting fibrin was polymerized to form a soft clot gel which adhered to the surface coated. The other side of the glass plates were coated identically.

The plates were then placed into heat defibrinated (57° C. for 3 minutes), citrated bovine or human plasma, recalcified with 1/10 vol. 1 M $CaCl_2$. Thrombin (20 units/milliliter of plasma) was added to activate the Factor XIII in the plasma which biochemically cross-linked the fibrin within 4-6 hours at room temperature to form a hard clotted fibrin. The plates were then washed extensively in IBS until the optical density at 280 nm was less than 0.02 indicating that most of the thrombin had been removed. The remaining amino groups on the fibrin were then reacted with an aqueous IBS solution containing 10 percent glutaraldehyde (by volume) at pH 7.4 for 2 hours, to make the fibrin substantially completely resistant toward fibrinolysis and to activate remaining amino groups for binding to a biochemically active enzyme. This formed the matrix on the glass plate.

The plates were then extensively washed in 0.15 M saline to remove excess glutaraldehyde. L-asparaginase (30,000 units in a solution of 600 ml IBS) was thereafter covalently bonded to the fibrin matrix on the plates (total of 1,500 IU L-asparaginase for each plate, 200 $cm^2$) by contacting the plates with the solution for a period of 4 to 12 hours. Excess L-asparaginase was washed out of the matrix and off of the plate with the above IBS solution until no traces of free enzyme could be detected.

Twenty plates (biochemically active members) were assembled in parallel within an enclosed cubicly-shaped housing of poly(methyl methacrylate) having side dimensions of 13×13 cm. and inlet and outlet ports to complete the organ. The organ was sterilized using an aquous 0.02 weight percent sodium azide solution in the housing and was stored with that solution at 4° C. with the inlet and outlet ports closed.

In Vitro Testing

After a thorough rinsing with saline until no sodium azide could be detected, one thousand milliliters of 10 mM L-asparagine solution in 0.15 M NaCl, 0.02 M sodium phosphate (phosphate buffered saline, "PBS") pH 7.4 was perfused through the organ at a flow rate of 200 milliliters/minute. Asparaginase activity was measured by ammonium quantitation with the Nessler's reagents see Roberts et al., J. Biol. Chem. 247: 84-90 (1972). At room temperature, the bio-artificial organ degraded 1,560 micro-moles of L-asparagine per minute per square meter of biochemically active member present (0.4 meters total) at room temperature. At 37° C. the organ degraded 4,050 micro-moles of L-asparagine per minute/$meter^2$.

In Vivo Testing

The bio-artificial organ was tested in healthy sheep with a carotid-jugular silastic shunt. The sheep was fully heparinized by a bolus of 20,000 USP units of heparin (Abbott), with a maintenance dose of 5,000 USP units/hour delivered by a micro pump. The system was primed with 600 millileters physiological saline. An extracorporeal blood flow (150 milliliters/minute) from the sheep was directed through the organ with the blood entering the organ from below.

A total of six animal experiments were performed with two reactors, each reactor being used for three experiments; however, no chemical data was taken on the third run of the second organ. Each reactor consisted of twenty biochemically active members in parallel array, as illustrated in FIG. 2, each active member having a biochemically active surface area of 200 $cm^2$.

The average animal experiment lasted for six hours and samples for L-asparagine determination (Beckman amino acid analyzer commercially available from Beckman of Redmond, Washington) were drawn from the arterial (inlet) side of the organ at 0,1,2, 5 and 6 hours of the experiment. The samples were used to determine possible leakage of L-asparaginase from the fibrin plates using a radioassay for assessing traces of free enzyme activity. See Cooney et al: "A Radiometric Method for the Measurement of 25 L-asparaginase at Concentrations Below $1 \times 10^{-5}$ I.U./ml: Technique and Application" Biocimia i, Medicini 15: 190/205 (1976).

The first organ degraded 760 micro moles of L-asparagine per minute/$meter^2$, and the second organ degraded 790 micro moles of L-asparagine/per minute/$meter^2$.

FIG. 3 shows a graph of the L-asparagine levels in the sheep averaged over the five experiments for which data were taken. As can be seen, after two hours the asparagine levels dropped to about 50 percent of its base line value and at the end of the six hour experiment about 70 percent of the circulating L-asparagine had been removed. At the same time, free L-asparaginase could not be detected at a concentration greater than $10^{-5}$ International units per milliliter of plasma.

Both organs showed fully maintained enzyme activity after three in vivo exposures. Both reactors were then stored in aqueous sodium azide at 4° C. as described above, and tested every two weeks for a period of three months. Neither reactor showed a decrease in enzyme activity during this period. The cross-linked fibrin polymer adhered tightly to the roughened glass plates and showed good mechanical stability towards the blood flow.

L-asparaginase bound to the organochemically cross-linked fibrin matrix exhibited only a moderate increase in $K_M$ value over free L-asparaginase, indicating a substantially preserved substrate affinity. The sheep showed a moderate decrease in platelet count.

Hematological workup consisted of a white blood cell count, hematocrit and platelet count determined at 0 hour, 1 hour and 5 hours from samples drawn at the venous (outlet) end of the organ.

Table I below shows the hemotological parameters investigated in the above-described organ tests. There was an overall expected, although, not dramatic, decrease of the platelet count (base line average: 443.600/microliter, average count after 6 hours 343.200/microliter, a drop of 22%). The white cell count showed an increase in experiments No. 2, 3 and 5 and a drop in Experiment No. 5. The hematocrit was decreased due to the dilution effect of priming the organ with saline.

TABLE I

Changes in White Blood Cell Count, Platelet Count and Hematocrit during in vivo Testing of Asparaginase-Containing Bio-Artificial Organ.

| Number of Test* | I | II | III | IV | V | |
|---|---|---|---|---|---|---|
| White Blood | 6.7 | 6.3 | 6.2 | — | 5.1 | Baseline |
| Cell Count | 6.0 | 6.7 | 9.1 | — | 3.9 | 1 hour |
| × 1000/microliter | 6.2 | 8.3 | 7.0 | — | 9.5 | 6 hours |
| Platelet Count | 300 | 352 | 470 | 533 | 563 | Baseline |
| × 1000/microliter | 310 | 476 | 488 | 501 | 460 | 1 hour |
|  | 294 | 250 | 420 | 375 | 440 | 6 hours |
| Hematocrit | 32 | 31 | 35 | — | 24 | Baseline |
|  | 29 | 27 | 28 | — | 18 | 1 hour |
|  | 28 | 25 | 24 | — | 18 | 6 hours |

*Tests numbered I, II and III were conducted using Organ 1, while tests number IV and V were conducted using Organ 2.

The meaning of the fluctuating white cell count, especially the increase, is unclear. White cell kinetics of sheep are different from human white cell kinetics, as shown in hemodialysis with Cuprophan membranes. Sheep do not exhibit the precipitous fall in white blood cell count within 30 minutes, as do humans.

EXAMPLE 2

Bio-Artificial Organs Containing Urease and Indolyl-3-Alkane-αHydroxylase

Four other organs were produced in accordance with the procedure of Example 1 except that for three of the organs, urease was substituted for the L-asparaginase, and indolyl-3-alkane-α-hydroxylase was substituted for L-asparaginase in the remaining organ. The results of in vitro tests of these bio-artificial organs of this invention at a blood flow rate of 200 milliliters/minute is shown below in Table II together with the results of the L-asparaginase tests of Example 1.

TABLE II

Moles Substrate Degradation/minute/meter$^2$
Enzyme-Fibrin Plate (Flowrate of 200 milliliters/minute)

|  |  | Room Temp. | 37 C. |
|---|---|---|---|
| 1 | UREASE-FIBRIN | 1250 | (3125) |
| 2 | UREASE-FIBRIN | 1700 | (4400) |
| 3 | UREASE-FIBRIN | 1500 | (3900) |
| 4 | INDOLYL-3-ALKANE-α-HYDROXYLASE-FIBRIN | 320 | |
| 5 | L-ASPARAGINASE-FIBRIN | 1560 | (4050) |

TABLE II-continued

Moles Substrate Degradation/minute/meter$^2$
Enzyme-Fibrin Plate (Flowrate of 200 milliliters/minute)

|  |  | Room Temp. | 37 C. |
|---|---|---|---|
| *6 | L-ASPARAGINASE-FIBRIN | 750 |  |
| *7 | L-ASPARAGINASE-FIBRIN | 790 |  |

*Tested in vivo

The high activity and stability exhibited by the fibrin-urease plates in the bio-artificial organs of this Example were observed for three weeks, and the observed activity and stability were remarkable since ethylenediamine tetraacetate (EDTA) was not present during use or storage. Previous experience indicated that it is difficult to stabilize insolubilized urease in the absence of EDTA.

The tryptophan degrading enzyme, indolyl-3-alkane-α-hydroxylase, also formerly posed difficult problems in maintaining activity as a matrix bound enzyme, because up to 95 percent of the enzymic activity was lost during the enzyme-matrix bonding process using a glutaraldehyde-activated amino argarose. Accordingly, fibrin provides an ideal micro environment which preserves and stabilizes the matrix-bonded enzymes.

EXAMPLE 3

Bio-Artificial Organ Containing A Biochemically Active Matrix Suspended In An Agarose Medium 200 Milliliters Low Temperature Electrophoresis Agarose (Bio-Rad) in a 4 percent weight in volume solution of a IBS at pH 7.35 was heated to 80° C. and then cooled to 40° C. This agarose gels irreversibly below about 37° C. Six percent weight in volume of 75 percent clottable fibrinogen (Pentex) in a solution of IBS was warmed to 40° C. and admixed with the agarose solution to form a composition. After 5 minutes of mixing, 10 ml. portions of the resulting composition were spread on roughened glass plates (10×10×0.1 cm. commercially available from LKB Instruments, Inc. of Vincent, Calif.) prewarmed to 37° C. The glass plates had been cleaned in nitric acid and coated with 0.5 percent agarose (Elphor coating procedure) to prevent clotting by blood exposure to glass. The plates were placed on an adjustable table with the plane of the table just reaching out of the water surface at a 37° C. water bath. The composition solidified in 10 minutes and adhered to the surface coated so that the reverse side could be coated identically.

The plates with composition solidified on both sides were dipped in a thrombin solution (commercially available as Thrombin, Topical from Parke-Davis) containing 20 units per milliliter in a solution of IBS. Degradation of fibrinogen to fibrin was carried out for one hour at room temperature. The cross-linking with Factor XIII and the remaining treating processes were carried out identically as described in Example No. 1 to produce an L-asparaginase-fibrin organ having twenty biochemically active members.

Before and after exposure of the organ to the extra-corporeal blood flow of sheep, maximal enzyme activity was measured by the conversion of L-asparagine (25 mM in phosphate buffered saline, PBS) to ammonia, ammonia determination by nesslerization. One liter of substrate solution was cycled through the organ at room temperature at a flow rate of 200 milliliters per minute. Ammonia was determined every ten minutes for thirty minutes.

FIG. 4 shows the results of testing on the bio-artificial organ after each successive use in vivo. As can be seen by FIG. 4, there was no decrease in the activity of the L-asparaginase indicating extraordinary stability of the chemical binding of the L-asparaginase.

$K_M$ determinations were carried out at room temperature on substrate solution ranging from 25 mM to 0.025 mM in 1,000 ml PBS pH 7.4 using the total organ. Data were plotted according to Lineweaver and Burk, (See Christensen et al. *Enzyme Kinetics* W. B. Saunders Co., 1967 pp. 68-91.) The fibrin insolubilized L-asparaginase exhibited a moderate increase in $K_M$ apparent to $2 \times 10^{-4}$ in comparison to the free enzyme having a $K_M$ of $3 \times 10^{-5}$. In vitro capacity at V max conditions was 300 micro moles of L-asparagine degraded per minute at 22° C., and 400 micro moles of L-asparagine degraded per minute at 37° C.

Shelf life was determined by weekly testing of the organs for up to 12 weeks under the V max conditions outlined above. No decrease in activity was detected during this period and there was only a 10 percent decrease after 8 months. In vitro testing of possible L-asparaginase leakage was carried out by cycling 1,000 ml. IBS or human plasma through the organ for 1 hour at room temperature. Every 15 minutes L-asparaginase activity was determined in solution using a sensitive spectrophotometric assay. See Cooney et al.: "A Spectrophotometric metric method for the simultaneous measurement of L-glutamine and L-asparagine in biological materials." Anal. Biochem. 40:312 (1971). Using IBS or plasma, no L-asparaginase could be detected in the solutions after 60 minutes (detection limit 1.0 International Units per liter per hour or 0.5 percent of total insolubilized enzyme activity.)

The organ was also tested under non-saturated substrate conditions to demonstrate substrate affinity to the insolublized L-asparaginase. One thousand milliliters of solution containing 5 mM of L-asparagine per milliliter were cycled through the organ at room temperatures. Determination of L-asparagine levels were carried out every 10 minutes. As can be seen in FIG. 5, there was a rapid clearance of the L-asparagine from aqueous solutions of IBS (I) and from bovine plasma (III) under non-saturated conditions indicating a high substrate affinity.

Animal experiments were carried out on healthy fully heparinized sheep with carotid-jugular shunts. The organ was extensively rinsed with sterile saline to remove sodium azide before use. The extracorporeal blood circulation entered the artificial organ from below and L-asparagine in the blood was determined on the arterial side of the organ. The in vivo clearance in sheep is shown in FIG. 5 as II. As can be seen, there was about a 40 percent reduction in the sheep's L-asparagine level after one hour and about a 65 percent reduction after two hours.

No toxic reactions were observed in any of the sheep in a total of 13 experiments. No antibodies could be detected after using the organ 3 times in the same sheep within a period of one month indicating low immunogenicity of the organ.

The foregoing specification is intended as illustrative and is not to be taken as limiting. Still other variations within the spirit and scope of this invention are possible and will readily present themselves to those skilled in the art.

What is claimed is:

1. A biochemically active matrix suitable for use in a bio-artificial organ comprising at least one biochemically active enzyme covalently bonded to the surface of a carrier matrix of organochemically cross-linked fibrin through a reactive group of the enzyme which is not essential for its enzymatic activity and suspended in a medium of agarose which irreversibly solidifies below 37° C.

2. The biochemically active matrix of claim 1 wherein the biochemically active enzyme is covalently bonded to the surface of the matrix by glutaraldehyde.

3. The biochemically active matrix of claim 1 wherein the biochemically active enzyme is L-asparaginase.

4. The biochemically active matrix of claim 1 wherein the biochemically active enzyme is urease.

5. The biochemically active matrix of claim 1 wherein the biochemically active enzyme is indolyl-3-alkane-α-hydroxylase.

6. The biochemically active matrix of claim 1 wherein said enzyme is asparaginase and is covalently bonded by glutaraldehyde.

7. A bio-artificial organ comprising:
   (a) a reactor housing defining an enclosed space with an inlet and an outlet, the inner surface of the housing being compatible with an extracorporeal blood flow;
   (b) a carrier matrix of organochemically cross-linked fibrin disposed within the reactor, said carrier matrix being suspended in a medium of agarose which gels irreversibly below 37° C.; and
   (c) a biochemically active enzyme covalently bonded to the surface of the matrix through a reactive group of the enzyme which is not essential for its enzymatic activity.

8. The bio-artificial organ of claim 7 wherein the biochemically active enzyme is covalently bonded to the surface of the matrix by glutaraldehyde.

9. The bio-artificial organ of claim 7 the biochemically active enzyme is L-asparaginase.

10. The bio-artificial organ of claim 7 wherein the carrier matrix is disposed on a physical support means.

* * * * *

UNITED STATES PATENT AND TRADEMARK OFFICE
CERTIFICATE OF CORRECTION

PATENT NO. : 4,438,198

DATED : March 20, 1984

INVENTOR(S) : Gottfried Schmer

It is certified that error appears in the above-identified patent and that said Letters Patent is hereby corrected as shown below:

Col. 6, line 54, "4-9" should be -- 4-8 --.

Col. 10, line 46, delete "25".

Signed and Sealed this

Thirteenth Day of November 1984

[SEAL]

Attest:

GERALD J. MOSSINGHOFF

Attesting Officer

Commissioner of Patents and Trademarks